United States Patent [19]

Marhold et al.

[11] Patent Number: 6,075,165
[45] Date of Patent: *Jun. 13, 2000

[54] PROCESS FOR THE PREPARATION OF POLYHALOGENATED BENZOTRIFLUORIDES, BENZOTRICHLORIDES AND BENZOYL CHLORIDES AND NEW TRIHALOGENOBENZOTRICHLORIDES AND -BENZOYL CHLORIDES

[75] Inventors: Albrecht Marhold, Leverkusen; Peter Andres, Leichlingen, both of Germany

[73] Assignee: Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/670,921

[22] Filed: Jun. 26, 1996

Related U.S. Application Data

[62] Division of application No. 08/180,949, Jan. 12, 1994, Pat. No. 5,599,980.

[30] Foreign Application Priority Data

Jan. 19, 1993 [DE] Germany .............................. 43 01 247

[51] Int. Cl.[7] .................................................. C07L 51/58
[52] U.S. Cl. ........................................... 562/859; 562/860
[58] Field of Search ..................................... 562/860, 859

[56] References Cited

U.S. PATENT DOCUMENTS

| | | | |
|---|---|---|---|
| 1,557,154 | 10/1925 | George | 562/859 |
| 1,880,169 | 9/1932 | Bennett et al. | 562/859 |
| 3,411,886 | 11/1968 | Burk | 562/859 |
| 4,276,231 | 6/1981 | Bockmann et al. | 562/859 |
| 4,582,948 | 4/1986 | Tang et al. . | |
| 4,588,726 | 5/1986 | Petersen et al. . | |
| 4,704,483 | 11/1987 | Tang et al. . | |
| 4,769,492 | 9/1988 | Kaieda et al. . | |
| 4,978,769 | 12/1990 | Kysela et al. . | |
| 5,072,038 | 12/1991 | Klauke et al. . | |
| 5,075,319 | 12/1991 | Lesher et al. . | |
| 5,169,853 | 12/1992 | Lesher et al. . | |
| 5,200,548 | 4/1993 | Klauke et al. . | |
| 5,599,980 | 2/1997 | Marhold et al. . | |

FOREIGN PATENT DOCUMENTS

| | | |
|---|---|---|
| 659239 | 8/1965 | Belgium . |
| 4496 | 3/1979 | European Pat. Off. . |
| 0004496 | 10/1979 | European Pat. Off. . |
| 4496 | 10/1979 | European Pat. Off. . |
| 0159388 | 10/1985 | European Pat. Off. . |
| 0354444 | 2/1990 | European Pat. Off. . |
| 820696 | 11/1937 | France . |
| 639578 | 11/1936 | Germany . |
| 639578 | 12/1936 | Germany . |
| 705650 | 5/1941 | Germany . |
| 2344603 | 3/1974 | Germany . |
| 3420796 | 12/1985 | Germany . |
| 3810093 | 10/1989 | Germany . |
| 4301247 | 7/1994 | Germany . | |
| 62-061948 | 5/1986 | Japan | C07C 51/38 |
| 1155350 | 7/1986 | Japan . | |
| 01025737 | 4/1987 | Japan | C07B 37/06 |
| 63-295529 | 5/1987 | Japan . | |
| 289534 | 12/1987 | Japan . | |
| 02145538 | 11/1988 | Japan | C07C 51/06 |
| 62-169446 | 1/1989 | Japan . | |
| 6413037 | 1/1989 | Japan . | |
| 04049263 | 6/1990 | Japan | B01J 31/02 |
| 04049264 | 6/1990 | Japan | B01J 31/02 |
| 1062301 | 3/1967 | United Kingdom . | |

OTHER PUBLICATIONS

K.V. Dvornikova, et al., Preparation of Polyfluorobenzotrihalides by the Reactions of Octafluorotoluene and its Derivatives With Aluminum Halides. Synthesis of Polyfluorostilbenes and Decafluorotolan, Plenum Publishing Corporation, pp. 525–532, (1991).

L. Andersen, et al., J. Chem. Soc. C., (1969), (2), 211–17.

Y. Pozdnyakovich, et al., J. Fluorine Chem., (1974), 4, (3), 283–96.

J. Bailey, et al., J. Fluorine Chem., (1987), 37, (1), 1–14.

Derwent Abstract of JP 61155350 (Jul. 15, 1986).

Derwent Abstract of JP 62289534 (Dec. 16, 1987).

L.P. Anderson, et al. Diels–Alder Reactions of Polyfluorocyclohexa–1,3–dienes. Part I. Addition of Alkynes to Perfluorocyclohexa–1,3–diene. A Route to ortho–Disubstituted Tetrafluorobenzenes J. Chem. Soc. C., (1969) pp. 211–217.

Bailey et al. Fluorinations with Complex Metal Fluorides. Part 9. Fluorinations of Toluene and Xylene Derivatives by Means of Caesium Tetrafluorocobaltate[III] Journal of Fluorine Chemistry, vol. 37, (1987) pp. 1–14.

Pozdnyakovich et al. Fluorine–containing Carbocations II. Polyfluorinated Benzyl Cations Journal of Fluorine Chemistry, vol. 4 (1974) pp. 283–286.

Derwent Abstract: Pharmaceuticals, p. 18, Week 9028, ASAG, B02, 90–214423/JO 2145–538–A; "Pharmaceuticals Intermediate Fluoro–benzoic Acids . . . ", Asahi Glass KK.

Derwent Abstract: General Chemistry, Week 8910, NICA, E14, 89–073118/10, JO 1025–737–A; "Prepn. of Halogenzene(s) and /or Halo–benzoic Acid(s) . . . ", Nippon Carbide Kogy KK.

(List continued on next page.)

*Primary Examiner*—Paul J. Killos
*Attorney, Agent, or Firm*—Sprung Horn Kramer & Woods

[57] ABSTRACT

Process for the preparation of polyhalogenated benzotrifluorides, benzotrichlorides and benzoyl chlorides and new trihalogeno-benzotrichlorides and -benzoyl chlorides Polyhalogenated benzotrifluorides can be reacted with chlorides from the series of Friedel-Crafts catalysts to give the corresponding benzotrichlorides, which can be hydrolysed by water in the presence of iron(III) chloride to give the corresponding benzoyl chlorides. These are suitable as intermediate products for the preparation of active compounds for medicaments and feed additives.

4 Claims, No Drawings

OTHER PUBLICATIONS

Derwent Abstract: Pharmaceuticals, p. 6, Week 8903, MITN, B05, 89–019649/03, J6 3295–529–A; "Prepn. of 2,3,4,5–Tetra:fluoro:benzoic Acid . . . ", Mitsubishi Gas Chem. KK.

Derwent Abstract: Pharmaceuticals, p. 5, Week 8717, WARN, B05, 87–102612/15, J6 2061–948–A; "Improved Route to 2,3,4,5–tetra: fluoro–benzoic acid . . . ", Warner–Lambert.

Chemical Abstracts of Japan, vol. 13, Abstract No. C07C63/70.

Chemical Abstracts, Abstract of De 2,344,603, Abstract No. 8638u (1974).

Japanese Patent Laid–Open Application (KOKAI) No. 1–13037–A (Ihara Chemical Ind. Co., Ltd.), Jan. 17, 1989.

PROCESS FOR THE PREPARATION OF POLYHALOGENATED BENZOTRIFLUORIDES, BENZOTRICHLORIDES AND BENZOYL CHLORIDES AND NEW TRIHALOGENOBENZOTRICHLORIDES AND -BENZOYL CHLORIDES

This application is a divisional of application Ser. No. 08/180,949, filed on Jan. 12, 1994, now U.S. Pat. No. 5,599,980.

The invention relates to a process for the preparation of 2,3,4,5-tetrafluoro-benzotrifluoride I from the corresponding ring-chlorinated benzotrifluorides by reaction with potassium fluoride, to a process for the preparation of polyhalogenated benzotrichlorides II from the corresponding benzotrifluorides I in the presence of chlorides from the series of Friedel-Crafts catalysts, to a process for the preparation of polyhalogenated benzoyl chlorides III from the benzotrichlorides II by partial hydrolysis and to new trihalogenobenzotrichlorides II and -benzoyl chlorides III (in the last case: Y=H).

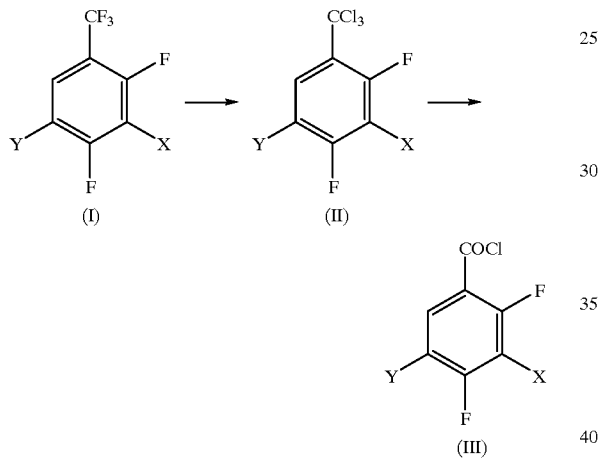

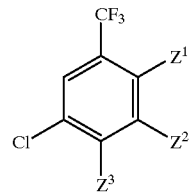

$X=Cl$ or F; $Y=H$ or F.

Polyhalogenated benzoyl halides are useful intermediate products for the preparation of antibacterial active compounds which can be used for the preparation of highly active medicaments (antiinfective agents); compare German Offenlegungsschrift 3 420 770 and EP-A 417 669.

According to German Offenlegungsschrift 3 420 796, 2,3,4,5-tetrafluorobenzoyl fluoride can be obtained from 2,3,4,5-tetrachlorobenzoyl fluoride by reaction with potassium fluoride; however, the yield is only 10%.

According to German Offenlegungsschrift 3 420 796, 2,4,5-trifluoro-3-chlorobenzoyl chloride can be obtained by chlorination of 2,4,5-trifluorobenzoic acid with chlorine and reaction of the resulting 2,4,5-trifluoro-3-chlorobenzoic acid with thionyl chloride.

It is known from J. Org. Chem. USSR 27 (1991) 525–532 that $CF_3$ groups on aromatics can be converted into $CCl_3$ groups by reaction with aluminium chloride.

An elegant route starting from the benzotrifluorides I which led to the benzoyl chlorides (III) via the benzotrichlorides II in a good yield has now been found.

The benzotrifluorides I to be employed as starting substances can be prepared from the corresponding tri/ tetrachlorobenzotrifluorides by chlorine/fluorine exchange with potassium fluoride.

The amount of potassium fluoride to be employed depends on the number of chlorine atoms to be exchanged. At least one mol of KF is employed per equivalent of chlorine, but in general 1.1–1.5 mol. A maximum of 2 mol of KF/equivalent of chlorine are used; beyond this, the amount of KF has practically no influence on the degree of fluorination and the process becomes uneconomical.

Solvents which can be employed for fluorination of the nucleus are the inert solvents known for fluorination reactions, for example dimethylformamide, dimethyl sulphoxide, N-methylpyrrolidone, diethyl sulphone and the like. However, tetramethylene sulphone (sulpholane) is particularly preferably employed.

The reaction temperature is between 160 and 260° C., depending on the desired degree of fluorination. While product which contains fluorine and chlorine on the nucleus is also found at the lower temperature, a quite significant proportion of the known 2,3,4,5-tetrafluorobenzotrifluoride is already formed at higher temperatures.

The invention relates, inter-alia, to a process for the preparation of 2,3,4,5-tetra-fluorobenzotrifluoride

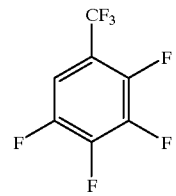

from the compounds of the formula wherein
$Z^1$, $Z^2$, $Z^3$, independently of one another represent fluorine or chlorine,
by reaction with potassium fluoride, optionally in the presence of a tetraphenylphosphonium or methyltriphenylphosphonium halide, preferably fluoride, chloride or bromide.

The above-mentioned tri-/tetrachlorobenzotrifluorides can be obtained in a simple manner and in high yields by chlorination of, for example, 4-chlorobenzotri-fluoride, while in contrast, chlorination of benzoyl chloride or 4-chlorobenzoyl chloride leads to numerous by-products which reduce the yield.

The invention thus relates to a process for the preparation of compounds of the formula II by reaction of compounds of the formula I with chlorides from the series of Friedel-Crafts catalysts. Suitable chlorides of this type are anhydrous and include, for example, aluminium chloride, titanium tetrachloride, silicon tetrachloride, antimony pentachloride and boron trichloride. The amount of Friedel-Crafts catalysts can vary within wide ranges; however, since on the one hand complete reaction of the starting compounds is desired, and on the other hand the intention is to avoid wasting chloride, as a rule 1 to 2, preferably 1 to 5 mol of chloride are employed per mol of benzotrifluoride I.

The reaction is preferably carried out in an organic solvent which is inert under the reaction conditions, for example in chlorobenzene, in chlorinated or brominated $C_1$–$C_4$-alkanes, such as methylene chloride or carbon tetrachloride, chloroform, 1,2,-dichloroethane, dibromomethane or bromoform, or in acetyl halides, such as acetyl chloride or bromide. However, the reaction can also be carried out in the absence of organic solvents.

The reaction temperature can be 0 to 150, preferably 10 to 100° C.

The invention furthermore relates to the compounds of the formula II.

The invention furthermore relates to a process for the preparation of compounds of he formula III by partial hydrolysis of compounds of the formula II with water in the presence of iron(III) chloride. The amount of water is in general 0.9 to 1.05 mol per mol of the compound II to be hydrolysed; to ensure a complete reaction and to avoid too substantial a hydrolysis, equimolar amounts of water are preferably employed. The iron(III) chloride can be employed in amounts of preferably 0.1 to 10, in particular 1 to 3% by weight, based on the compound II to be hydrolysed. The reaction can be carried out in the presence or absence of solvents. Suitable solvents are those inert organic solvents which have a suitable boiling point, such as, for example, chlorobenzene. The reaction temperature can be 80 to 140° C.

The invention furthermore relates to compounds of the formula III wherein Y represents H.

The invention furthermore relates to a process for the preparation of compounds of the formula III from compounds of the formula I by combination of the process steps described above. This process has the advantage over the hydrolysis of the compounds I, which is likewise conceivable, to give the corresponding benzoic acid and subsequent reaction with benzoyl chloride, that production of large amounts of fluoride-containing sulphuric acid is avoided. The aluminium fluoride obtained in the first part step of the process according to the invention is insoluble and can be disposed of by landfill directly in the form obtained.

The compounds I and II according to the invention are suitable for the preparation of active compounds for medicaments and feed additives. For example, 8-chloro-1-cyclopropyl-7-fluoro-1,4-dihydro-4-oxo-3-quinoline-carboxylic acid can be obtained from 3-chloro-2,4-difluoro-benzoyl chloride (compound II; X=Cl, Y=H) by the following multi-stage process:

Reaction of 3-chloro-2,4-difluoro-benzoyl chloride with diethyl malonate gives diethyl (3-chloro-2,4-difluoro-benzoyl)-malonate, and partial hydrolysis and decarboxylation lead to ethyl (3-chloro-2,4-difluoro-benzoyl)-acetate, which is reacted with ethyl orthoformate/acetic anhydride to give ethyl 2-(3-chloro-2,4-difluorobenzoyl)-3-ethoxy-acrylate; further reaction with cyclopropylamine leads to ethyl 2-(3-chloro-2,4-difluoro-benzoyl)-3-cyclopropylaminoacrylate, which is cyclized with potassium carbonateldimethylformamide to give ethyl 8-chloro- 1-cyclopropyl-7-fluoro-1,4-dihydro-4-oxo-3-quinolinecarboxylate; hydrolysis then finally leads to the corresponding carboxylic acid. The reaction sequence described can be represented by the following equation:

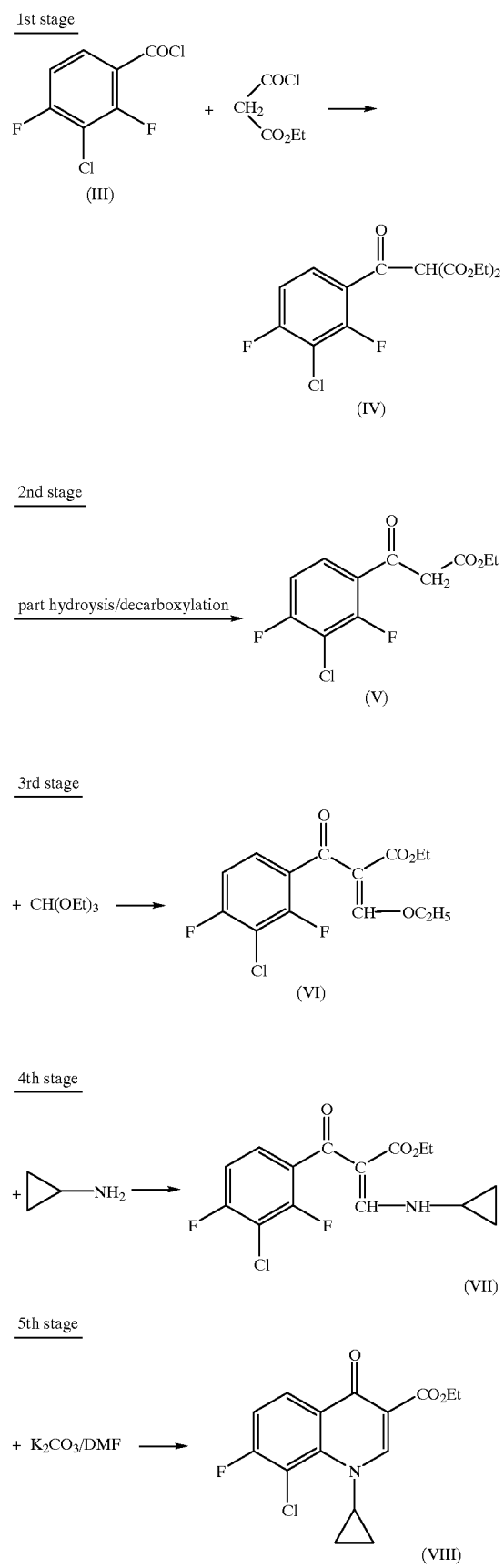

6th stage

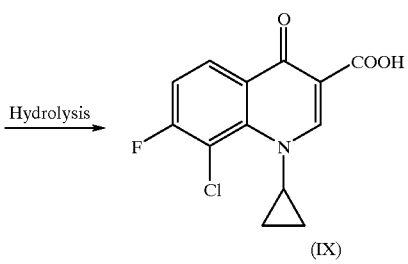

Hydrolysis

The quinolonecarboxylic acid obtained in the 6th stage can be converted by reaction with compounds Z—H of the formulae

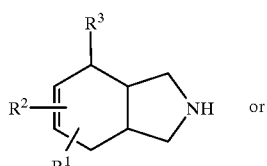

(X)

or

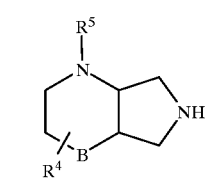

(XI)

wherein
- $R^1$ represents hydrogen, straight-chain or branched $C_1$–$C_3$-alkyl or cyclopropyl,
- $R^2$ represents hydrogen or methyl,
- $R^3$ represents hydrogen, hydroxyl, —$NR^6R^7$, hydroxymethyl or —$CH_2NR^6R^7$,
- $R^4$ represents hydrogen, methyl or radicals having the structures —CH=CH— $CO_2R'$, —$CH_2$—$CH_2$—$CO_2R'$, —$CH_2$—CO—$CH_3$ or —$CH_2$—$CH_2$—CN,
- $R^5$ represents hydrogen or methyl,
- $R^6$ represents hydrogen, optionally hydroxyl-substituted $C_1$–$C_3$-alkyl, alkoxycarbonyl having 1 to 4 C atoms in the alkoxy part or $C_1$–$C_3$-acyl,
- $R^7$ represents hydrogen or methyl,
- R' represents methyl or ethyl and
- B represents —$CH_2$—, —O— or a direct bond, into quinolonecarboxylic acid derivatives of the formula

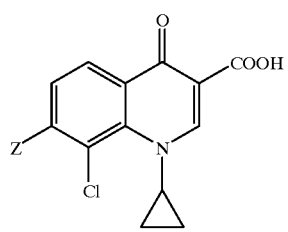

(XII)

The compounds are active compounds having an excellent antibacterial action.

EXAMPLES

A. Preparation of the starting compounds 2,3,4-Trichloro-benzotrifluoride a) 2,900 ml of hydrogen fluoride are initially introduced into a V4A autoclave at 0–10° C., and 40 ml of titanium tetrachloride and a mixture of 900 g of 1,2,3-trichlorobenzene and 2,400 ml of carbon tetrachloride are then metered in. After the autoclave has been closed, it is heated at 140° C. for 15 hours under the autogenous pressure (122 bar towards the end). After cooling to room temperature, the mixture is slowly let down in water. The residual hydrogen fluoride is then distilled off and the reaction mixture is washed with water, dried and likewise distilled. 975 g of 2,3,4-trichlorobenzotrifluoride are obtained (boiling point 96–99° C./18 mbar, $n_D^{20}$=1.5040).

3-Chloro-2,4-difluoro-benzotrifluoride 3,700 g of potassium fluoride are initially introduced into 10,000 ml of tetramethylene sulphone in a stirred apparatus with exclusion of moisture, and 500 ml of tetramethylene sulphone are distilled off under a pressure of 16 mbar. 3,965 g of 2,3,4-trichlorobenzotrifluoride are then metered in and the mixture is heated to 230° C. The product formed is taken off via a column with a reflux divider. After three hours, a slight vacuum is applied and the mixture is subjected to incipient distillation up to the boiling point of tetramethylene sulphone. The coarse distillate (3,390 g) is subjected to fine distillation. The first runnings of 396 g comprise mainly 2,3,4-trifluoro-benzotrifluoride (boiling point 92–142° C.; the main runnings (3,951 g) have a boiling point of 142–143° C. and comprise 3-chloro-2,4-difluoro-benzotrifluoride to the extent of 97.6%.

2,3,4,5-Tetrachloro-benzotrifluoride 1 kg of 4-chlorobenzotrifluoride are initially introduced into a stirred apparatus with a gas take-off to a destruction tower, and 15 g of powdered iron sulphide are added. Chloride is then passed in at 60° C. and the temperature is increased at the rate at which the chlorine is taken up, until the end point of 110° C. is reached. The end point is determined by gas chromatography analysis. Distillation gives, after first runnings of benzotrifluorides of low degree of chlorination, 894 g of 2,3,4,5-tetrachloro-benzotrifluoride having a boiling range of 112–115° C./20 mbar.

2,3,4,5-Tetrafluoro-benzotrifluoride a) A mixture of 852 g of 2,3,4,5-tetrachloro-benzotrifluoride (3 mol), 1,044 g of potassium fluoride (18 mol), 60 g of crown ether (18 ring members, 6 oxygen atoms) and 2,050 ml of tetramethylene sulphone was stirred at a temperature of 240° C. under a nitrogen atmosphere (5 bar) for 15 hours; during this period, the pressure rose to a maximum of 12 bar. Volatile constituents were distilled off under normal pressure up to an internal temperature of 180° C. Towards the end of the distillation, a vacuum was applied; as soon as tetramethylene sulphone passed over, the distillation was interrupted. The coarse distillate (495 g) was redistilled over a column; 387 g of 2,3,4,5-tetrafluoro-benzotrifluoride were obtained.

b) 835 g (14.4 mol) of potassium fluoride in 1440 ml of tetramethylene sulphone are initially introduced into a stirred V4A-steel apparatus and the solvent is distilled off (100 ml) for drying under a pressure of 20 mbar. Then 852 g (3 mol) of 2H-tetrachlorobenzotrifluoride and 42 g of tetraphenylphosphonium bromide are added. Then the mixture is heated to 210° C. for 18 hours under the autogenous pressure (3.5 bar). At the end of the reaction the pressure is gradually released and the product is delivered with expansion into a cooled receiver via a cooler. Finally the remaining product is distilled off at reduced pressure (up to 20 mbar) up to the boiling point of the solvent. A total of 538 g of distillate are obtained which, according to analysis by gas chromatography, contain 407 g =62% yield of 2H-tetrafluorobenzotrifluoride and 126 g (17.9% yield) of 5-chloro-2,3,4-trifluorobenzotrifluoride.

c) The reaction is carried out as in b), except that 3 bars of nitrogen are applied prior to heating the mixture and a total pressure of 6 bar forms at 210° C. Working up yields 585 g of a coarse distillate which contains 400 g (61.1%) of 2H-tetrafluorobenzotrifluoride and 170 g of 5-chloro-2,3,4-trifluorobenzotrifluoride. The recovery rate of fluorinated benzotrifluorides is 85.3%.

d) 812 g (14 mol) of potassium fluoride and 1400 ml of tetramethylene sulphone are subjected to incipient distillation at 20 mbar (quantity of distillate: 100 ml) in a stirred V4A steel apparatus. Then 40 g of tetraphenylphosphonium bromide and a mixture of 795 g (2.8 mol) of 2H-tetrachlorobenzotrichloride and 170 g (0.78 mol) of 5-chloro-2,3,4-trifluorobenzotrifluorde are added and the mixture is stirred for 18 hours at 210° C. under the autogenous pressure (max. pressure 3.4 bar). Distillation yields 747 g of a crude distillate which is redistilled in a rotating strip column. 396 g of 2H-tetrafluorobenzotrifluoride and 318 g of 5-chloro-2,3,4-trifluorobenzotrifluoride are obtained. The recovery rate of the isolated yield is 90.5%.

e) Reaction b) is repeated, identical starting quantities being stirred at 200° C. instead of 210° C. and for 24 h (instead of the 18 hours of reaction b). Working up by distillation yields 596 g of a crude distillate containing 353 g (54%) of 2H-tetrafluorobenzotrifluoride and 239 g (34%) of 5-chloro-2,3,4-trifluorobenzotrifluoride. The recovery rate is 88%.

3-Chloro-2,4-difluoro-benzotrifluoride 800 g of potassium fluoride and 2500 ml of tetramethylene sulphone are initially introduced into a stirred apparatus and the mixture is subjected to incipient distillation under a pressure of 15 mbar until about 200 ml of solvent have passed over. 1100 g of 2,3,4-trichlorobenzotrifluoride are then metered in at a temperature of 150° C. and the mixture is heated to 220° C. with exclusion of moisture. The product is taken off over a column with a reflux divider; the mixture is kept at this temperature for a total of 12 hours. The content of fluoroaromatics is then distilled off under reduced pressure. After redistillation of the reaction mixture, 652 g of 3-chloro-2,4-difluoro-benzotrifluoride are obtained, after first runnings comprising 2,3,4-trifluoro-benzotrifluoride, in a boiling range of 37–40° C./16 mbar.

2,3,4-Trifluoro-benzotrifluoride

An HC4 autoclave is charged with 928 g of potassium fluoride and 3,200 ml of N-methyl-pyrrolidone and the mixture is subjected to incipient distillation in vacuo for drying. 1,732 g of 3-chloro-2,4-difluorobenzotrifluoride are then added with exclusion of moisture, nitrogen is forced in to a pressure of 5 bar and the mixture is heated at 270° C. for 10 hours, while stirring. After cooling, the mixture is let down and is distilled under a slight vacuum up to the boiling point of the N-methyl-pyrrolidone. Fine distillation of the crude distillate gives 439 g of 2,3,4-trifluorobenzotrifluoride, boiling point: 104–105° C., and 881 g of unreacted starting material, which can be employed again for the fluorination.

B. Process/compounds according to the invention 2,3,4,5-Tetrafluoro-benzotrichloride 85 g (0.64 mol) of aluminiumn chloride (anhydrous) are initially introduced into 500 ml of methylene chloride, and 109 g (0.5 mol) of 2,3,4,5-tetrafluoro-benzotrifluoride are added dropwise at room temperature, while stirring. The, mixture is then subsequently stirred at 40° C. for 1 hour, allowed to cool and poured onto 600 g of ice, the organic phase is separated off, the aqueous phase is extracted with ether and the combined phases are washed with water and dried over anhydrous magnesium sulphate. After concentration, the residue is distilled. 108.3 g (81% of theory) of product are obtained; boiling point: 89–90° C./22 mbar.

2,3,4,5-Tetrafluoro-benzovl chloride 802 g of 2,3,4,5-tetrafluoro-benzotrichloride are initially introduced into a stirred apparatus, and 8 g of $FeCl_3$ are added. Water is slowly metered in under the surface of the starting material at 120° C. (54 g of water in total). Vigorous evolution of hydrogen chloride immediately starts. The hydrogen chloride is passed to a destruction tower via the condenser. The mixture is stirred until the evolution of gas has ended. The product is then distilled. 569 g of 2,3,4,5-tetrafluoro-benzoyl chloride are obtained (89.4% of theory), boiling point: 80–82° C./18 mbar.

2.3,4-Trifluoro-benzoyl chloride 221 g of 2,3,4-trifluoro-benzoyl chloride are obtained from 312 g of 2,3,4-trifluoro-benzotrichloride analogously to the above instructions; boiling point 78–79° C./15 mbar.

3-Chloro-2,4-difluoro-benzotrichloride 216.5 g of 3-chloro-2,4-difluoro-benzotrifluoride in 440 ml of methylene chloride are initially introduced into a stirred apparatus, and 150 g of $AlCl_3$ are introduced in small portions. The reaction is slightly exothermic. When the addition has ended, the mixture is heated under reflux (42° C.) for 2 hours, cooled and poured onto 1 l of ice-water. After intensive thorough mixing, the mixture is filtered over a suction filter and the organic phase is then separated off. After drying, the methylene chloride phase is distilled. 231 g of 3-chloro-2,4-difluoro-benzotrichloride with a boiling range of 124–126° C./18 mbar are obtained.

3-Chloro-2,4-difluoro-benzoyl chloride 266 g of 3-chloro-2,4-difluoro-benzotrichloride are initially introduced into a stirred apparatus together with 4 g of $FeCl_3$. The mixture is heated to 110° C. and 18 g of water are slowly metered into the bottom through a capillary. The hydrogen chloride formed is passed to a destruction unit via an intensive condenser. When the addition and the evolution of gas have ended, the mixture is cooled and the crude product is distilled. 195 g of 3-chloro-2,4-difluoro-benzoyl chloride pass over in the boiling range of 108–110° C./22 mbar ($n_D^{20}$: 1.5362).

C. Further Processing of the compounds according to the invention

C.1 a) Diethyl (3-chloro-2,4-difluorobenzoyl)malonate 3.9 g (0.16 mol) of magnesium are initially introduced into 8.6 ml of ethanol and the reaction is started with carbon tetrachloride. A solution of 23.1 g (0.144 mol) of diethyl malonate in 16.3 ml of ethanol is added dropwise at an internal temperature of 50–60° C. such that this temperature is maintained. The mixture is then subsequently stirred at 60° C. for one hour. Thereafter, a solution of 31.3 g (0.148 mol) of 3-chloro-2,4-difluorobenzoyl chloride in 16 ml of toluene is added dropwise at −10 to −5° C. and the mixture is subsequently stirred at 0° C. for one hour and then overnight, while warming to room temperature. The reaction mixture is poured onto ice-water, acidified with 10 ml of concentrated sulphuric acid and extracted with toluene. The extract is washed with saturated sodium chloride solution and the solvent is removed in vacuo. Crude yield: 49.9 g b) Ethyl (3-chloro-2,4-fluorobenzoyl)acetate 49.9 g of the crude product obtained under a. are heated under reflux in 60 ml of water with 1.83 g of p-toluenesulphonic acid for 4.5 hours. The cooled mixture is extracted with methylene chloride, washed with saturated sodium chloride solution, dried over sodium sulphate and concentrated in vacuo. Crude yield: 37.3 g c) Ethyl 2-(3-chloro-2,4-difluorobenzoyl)-3-ethoxyacrylate 37.3 g of the crude product obtained under b. are heated at 150–160° C. with 33.4 g (0.226 mol) of ethyl orthoformate and 37.2 g (0.365 mol) of acetic anhydride for two hours. Excess reagent is removed first in vacuo and then under a high vacuum up to a bath temperature of 100° C. Crude yield: 40.2 g d) Ethyl 2-(3-chloro-2,4-difluorobenzoyl)-3-cyclopropylaminoacrylate 40.2 g of the crude product obtained under c. are dissolved in 100 ml of ethanol, and 9.6 g (0.168 mol) of cyclopropylamine are added dropwise, while cooling in an ice bath. The reaction mixture is subsequently stirred at room temperature for 30 minutes and 100 ml of ice-water are then added. The product which has precipitated is isolated, washed with water and dried at 100° C. Yield: 30.8 g (63% of theory, based on (c)) Melting point: 101–104° C.

e) Ethyl 8-chloro-1-cyclopropyl-7-fluoro-1,4-dihydro-4-oxo-3-quinolinecarboxylate 15 g (0.046 mol) of the crude product obtained under d. are heated at 140–150° C. in 90 ml of dimethylformamide with 7.2 g (0.052 mol) of potassium carbonate for two hours. The cooled mixture is poured onto water and the product is isolated, washed with water and dried at 100° C. Yield: 13.5 g (95% of theory) Melting point: 149–153° C.

f) 8-Chloro-1-cyclopropyl-7-fluoro-1,4-dihydro-4-oxo-3-quinolinecarboxylic acid

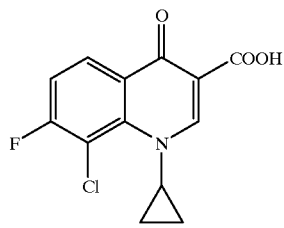

13.5 g (0.044 mol) of the ester obtained under e. are heated under reflux in a mixture of 52 ml of acetic acid, 52 ml of water and 5.2 ml of concentrated sulphuric acid for four hours. The cooled mixture is poured onto ice-water and the product is isolated, washed thoroughly with water and dried at 100 ° C. Yield: 11.6 g (94% of theory) Melting point: 192–193° C.

7-(4-Amino-1,3,3a,4,7,7a-hexahydroisoindol-2-yl)-8-chloro-1-cyclopropyl-1,4-dihydro-4-oxo-3-quinolinecarboxylic acid

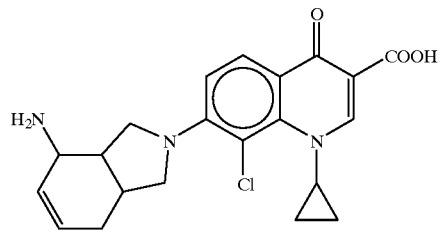

1.26 g (4.5 mmol) of 8-chloro-1-cyclopropyl-7-fluoro-1,4-dihydro-4-oxo-3-quinolinecarboxylic acid are heated at 100° C. with 0.75 g (5.4 mmol) of 4-amino-1,3,3a,4,7,7a-hexahydroisoindole and 1.01 g (9 mmol) of 1,4-diazabicyclo[2.2.2]octane in 45 ml of dimethyl sulphoxide for one hour. All the volatile components are removed under a high vacuum and the residue is stirred thoroughly with acetonitrile and dried at about 100° C. Yield: 1.7 g (94% of theory) Melting point: 184–186° C. (with decomposition).

C.2 a) Diethyl (2,3,4-trifluorobenzoyl)malonate 3.6 g (0.148 mol) of magnesium filings are initially introduced into 8.1 ml of ethanol, the reaction is started with a few drops of carbon tetrachloride, and a solution of 21.8 g (0.136 mol) of diethyl malonate in 15 ml of ethanol and 58 ml of toluene is then added dropwise such that the internal temperature is between 50 and 60° C. The mixture is then subsequently stirred at 60° C. for one hour. A solution of 27.6 g (0.15 mol) of 2,3,4-trifluorobenzoyl chloride in 15.4 ml of toluene is added dropwise at −10 to −5° C. and the mixture is subsequently stirred at 0° C. for one hour and then overnight, while warming to room temperature. It is poured onto 60 ml of ice-water, 9.7 ml of concentrated sulphuric acid are added and the mixture is extracted with toluene. The extract is washed with saturated sodium chloride solution and the solvent is removed in vacuo. Crude yield: 45.2 g b) Ethyl (2,3,4-trifluorobenzoyl)acetate 45.2 g of the crude product obtained in a. are heated under reflux in 57 ml of water with 1.66 g of p-toluenesulphonic acid for 4.5 hours. The cooled mixture is extracted with methylene chloride, washed with saturated sodium chloride solution, dried over sodium sulphate and concentrated in vacuo. Crude yield: 33 g c) Ethyl 3-ethoxy-2-(2,3,4-trifluorobenzoyl)acrylate 33 g of the product obtained under b. are heated at 150–160° C. with 31.5 g (0.213 mol) of ethyl orthoformate and 31.5 g (0.344 mol) of acetic anhydride for two hours. Excess reagent is removed first in vacuo and then under a high vacuum up to a bath temperature of 100° C. Crude yield: 34.5 g d) Ethyl 3-ethylamine-2-(2,3,4-trifluorobenzoyl)-acrylate 9.06 g (0.03 mol) of the product obtained under c. are initially introduced into 60 ml of ethanol at 0° C., and 2.12 ml (0.033 mol) of a 70% strength ethylamine solution are added dropwise. The mixture is subsequently stirred at room temperature for four hours, 60 ml of water are added dropwise and the product which has precipitated is isolated. It is washed with water and dried at about 100° C. Yield: 5.0 g (55% of theory) Melting point: 106–108° C.

e) Ethyl 1-ethyl-7,8-difluoro-1,4-dihydro-4-oxo-3-quinolinecarboxylate 5.0 g (0.017 mol) of the product obtained under d. are heated at 100° C. with 2.6 g (0.019 mol) of potassium carbonate in 30 ml of dimethylformamide for four hours. The cooled mixture is poured onto ice-water and the product is isolated, washed with water and dried at 100° C. Yield: 3.6 g (77% of theory) Melting point: 164–166° C.

f) 1-Ethyl-7,8-difluoro-1,4-dihydro-4-oxo-3-quinolinecarboxylic acid 3.5 g of the product obtained under e. are heated at 140° C. in a mixture of 16 ml of acetic acid, 16 ml of water and 1.6 ml of concentrated sulphuric acid for four hours. The cooled mixture is poured onto ice-water and the product which has precipitated is isolated, washed with water and dried at 100° C. Yield: 3.0 g (99% of theory) Melting point: 237–239° C.

The product f) can be reacted with an amine Z—H to give the corresponding quinolonecarboxylic acid derivative.

We claim:

1. A process for the preparation of a compound of the formula

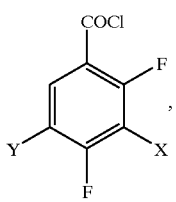

(III)

wherein

X is Cl or F, and

Y is H or F, which comprises reacting a compound of the formula

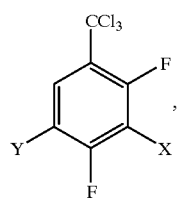

(II)

with water in the presence of iron (III) chloride.

2. The process according to claim 1, wherein there are employed 0.9 to 1.05 mols of water per mol of compound II.

3. The process according to claim 1, wherein the iron (III) chloride is present in about 0.1 to 10% the weight of compound II.

4. A process for the preparation of a compound of the formula

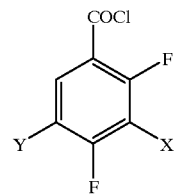

wherein

X is Cl or F, and

Y is H or F, which comprises reacting a compound of the formula

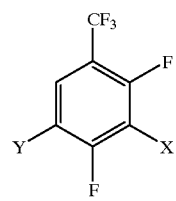

in methylene chloride or chlorobenzene at about 0 to 150° C. with a Friedel-Crafts chloride catalyst, thereby to produce a compound of the formula

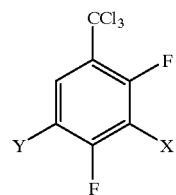

and reacting such compound with water in the presence of iron (III) chloride.

* * * * *